United States Patent [19]
Denhardt et al.

[11] Patent Number: 5,695,761
[45] Date of Patent: Dec. 9, 1997

[54] SUPPRESSION OF NITRIC OXIDE PRODUCTION BY OSTEOPONTIN

[75] Inventors: David T. Denhardt, Bridgewater; Shiaw-Min Hwang, Piscataway; Diane Elaine Heck, Rumson; Cecilia Ang Lopez, North Brunswick; Debra L. Laskin, Basking Ridge; Jeffrey D. Laskin, Piscataway, all of N.J.

[73] Assignees: Rutgers University, Piscataway; University of Medicine & Dentistry of NJ, Newark, both of N.J.

[21] Appl. No.: 173,116

[22] Filed: Dec. 23, 1993

[51] Int. Cl.$^6$ ............ A01N 37/18; A61K 38/00; A61K 39/38; C07K 2/00

[52] U.S. Cl. ............ 424/184.1; 424/85.5; 424/278.1; 530/351; 530/330; 530/326; 530/300; 514/2; 514/12

[58] Field of Search ............ 424/88, 85.5, 278.1, 424/184.1; 530/351, 330, 326, 300; 514/2, 12

[56] References Cited

U.S. PATENT DOCUMENTS

| | | |
|---|---|---|
| 5,049,659 | 9/1991 | Cantor et al. |
| 5,281,627 | 1/1994 | Griffiths |
| 5,312,835 | 5/1994 | Kilbourn et al. |

OTHER PUBLICATIONS

Denhardt and Guo, 1993, FASEB J. 7:1475–82.
Goureau et al., 1993, Proc. Natl. Acad. Sci. U.S.A. 90:4276–80.
Ignarro et al., 1993, Proc. Natl. Acad. Sci. U.S.A. 90:8103–07.
Lopez et al., 1993, Lab. Invest. 69:355.
Markewitz et al., 1993, J. Clin. Invest. 91:2138–2143.
Zimolo et al., 1994, Am. J. Physiol. :C376–80.
Chambers et al., 1992, Anticancer Res. 12:43–48.
Heck et al., 1992, J. Biol. Chem. 267:21277–80.
Lyons, 1992, J. Biol. Chem. 267:6370–74.
McCall et al., 1992, Biochem. Biophys. Res. Commun. 186:680–685.
Punjabi, et al., 1992, J. Immunol., 149:2179–84.
Nathan, 1992, FASEB J. 6:3051–64.
Stoos et al., 1992, J. Clin. Invest. 89:761–765.
Wilcox et al., 1992, Proc. Natl. Acad. Sci. USA 89:11993–97.
Ishii et al., 1991, J. Pharmacol. Exp. Therap. 256:38–43.
Miyanchi et al., 1991, J. Biol. Chem. 266:20369–74.
Ding et al., 1990, J. Immunol. 145:940–44.
Craig et al., 1989, J. Biol. Chem. 264:9682–9.
Khokha and Denhardt, 1987, Anticancer Res. 7:653–660.
Oldberg et al., 1986, Proc. Natl. Acad. Sci. U.S.A., 83:8819–23.
Oliphant et al., 1986, Gene 44:177.
Green et al., 1982, Analytical Biochem. 126:131–138.

*Primary Examiner*—Paula K. Hutzell
*Assistant Examiner*—N. M. Minnifield
*Attorney, Agent, or Firm*—Klauber & Jackson

[57] ABSTRACT

The present invention relates to compositions and methods for inhibition of the vasoactive and signal transduction agent nitric oxide (NO), and to therapeutic treatment of diseases or disorders that involve inappropriate or detrimental NO activity. The invention particularly relates to modulation of kidney function. In specific embodiments, osteopontin and a 20-amino acid fragment of osteopontin that contains an Arg-Gly-Asp sequence suppress expression of inducible NO synthase mRNA, and osteopontin suppresses the activity of constitutive NO synthase.

18 Claims, 7 Drawing Sheets

SUPPRESSION OF NITRIC OXIDE PRODUCTION BY OSTEOPONTIN

This research leading to this invention was supported in part by funds from National Institution of Health Grant Nos. AG07972, DC01295, ES047038, GM34310, ES03647 and ES05022. The Government may have certain rights in the invention.

FIELD OF THE INVENTION

The present invention relates to compositions and methods for inhibition of the vasoactive and signal transduction agent nitric oxide (NO), and to therapeutic treatment of diseases or disorders that involve inappropriate or detrimental NO activity. Thus, the invention relates to modulation of cellular activities, including macrophage activity, endothelial cell function, and the like. In a specific aspect, the invention relates to modulation of kidney function.

BACKGROUND OF THE INVENTION

If blood pressure is not maintained within normal limits serious pathologies develop. For example, the hypertension characteristic of vascular disease or the hypotension that accompanies septic shock can result. The vascular musculature can respond to modulate immediate changes in blood pressure, while longer term adjustments are made in a kidney.

Several homeostatic processes cooperate to regulate blood pressure. In particular, angiotensin (A II) is an important vasoconstrictor produced by kidney proximal tubule epithelial cells (Yanagawa et al., 1991, Kidney Int. 39:938–941). At the same time, angiotensin induces nitric oxide production. Nitric oxide induces vasodilation. It appears that angiotensin acts to decrease blood flow, and at the same time induces NO production as a negative feedback regulator to counterbalance the action of the angiotensin. The two regulators act to balance each other and keep blood pressure within normal limits.

Nitric Oxide

Nitric oxide (NO), also known as endothelium-derived relaxing factor (EDRF), is a potent vasodilator produced by many different types of cells and tissues, such as endothelium, macrophages and neuronal cells (reviewed by Lowenstein and Snyder, 1992, Cell 70:705–707; Nathan, 1992, FASEB J. 6:3051–64). NO production can be very important in specific organs such as the brain and kidneys. For example, many different types of kidney cells, including tubule epithelial cells (Ishii et al., 1990, Can. J. Physiol. Pharmacol. 68:749–751), glomerular endothelial cells (Marsden et al., 1990, J. Exp. Med. 172:1843–52; Shultz et al., 1991, Am. J. Physiol. 261:F600–F606), and mesangial cells (Pfeilschifter and Vosbeck, 1991, Biochem. Biophys. Res. Commun. 175:372–379) produce NO. Cells that respond to NO include macula densa (Wilcox et al., 1992, Proc. Natl. Acad. Sci. U.S.A. 89:11993–97) and juxtamedullary afferent and efferent arterioles (Ohishi et al., 1992, Am. J. Physiol. 363:F900–F906; Ito et al., 1993, J. Clin. Invest. 91:2012–19). Both A II (the x-mer peptide produced by cleavage of angiotensinogen) and NO play an important role in the regulation of blood flow, renal hemodynamics and tubular transport (Radermacher et al., 1992, Kidney Int. 41:1549–59; Yanagawa et al., 1991, supra). Considerable evidence suggest that NO and A II (or more accurately, the renin-angiotensin system) interact with each other to control the vascular functions and homeostasis of fluid in kidney (Ohishi et al., 1992, supra).

NO synthesized by nitric oxide synthase (NOS) from arginine and oxygen is also an important signal transducing molecule in various cell types (Nathan, 1992, FASEB J. 6:3051–64). In the brain it mediates the excitatory effect of glutamate. In the vascular endothelium, NO was characterized as endothelium-derived relaxing factor because it promoted vascular smooth muscle relaxation. In mouse macrophages it has assumed, under certain situations, the role of a cytotoxic agent—a reactive nitrogen intermediate that is lethal to cancer cells and microorganisms.

As a signal transducer, its best understood effector molecule is guanylyl cyclase, which it activates. Increased intracellular cGMP in turn impacts on a variety of biochemical pathways, for example those involving cGMP-dependent protein kinases.

Nitric oxide inhibits iron-containing enzymes important in respiration and DNA synthesis. It combines with superoxide to form peroxynitrite, which decomposes to the reactive $NO_2$ and hydroxyl radicals, and it stimulates ADP-ribosylation of various proteins including glyceraldehyde-3-phosphate dehydrogenase, with consequent inactivation.

NO, because it contributes to blood flow regulation by setting the degree of relaxation of vascular smooth muscle cells, is critical to the maintenance of normal kidney function. It assures adequate oxygenation of the renal medulla (Brezis et al., 1991, J. Clin. Invest. 88:390–395) and regulates glomerular capillary pressure (Wilcox et al., 1992, Proc. Natl. Acad. Sci. U.S.A. 89:11993–97). NO produced by endothelial cells can inhibit sodium transport by cortical collecting ducts (Stoos et al., 1992, J. Clin. Invest. 89:761–765). Tubule epithelial cells appear to contain both a constitutive form of NOS (Ishii et al., 1991, J. Pharmacol. Exp. Therap. 256:38–43), and a form that can be induced by $TNF\alpha$ and $IFN\gamma$ in both proximal tubule cells and inner medullary collecting duct cells (Markowitz et al., 1993, J. Clin. Invest. 91:2138–2143). Since NO can exert a cytotoxic action both on cells that produce it and on neighboring cells, it is important that its production be subject to fairly close regulation.

Inhibitors of NO synthesis, such as N-nitro-L-arginine (L-NNA) and N-monomethyl-L-arginine (L-NMA), can cause a significant reduction in glomerular flow rate and glomerular filtration rate and increase renal vascular resistance (Radermacher et al., 1992, supra; Gardner et al., 1990, Hypertension 15:486–492) in perfused kidney; these inhibitors can also reduce the diameter of arterioles (Ito et al., 1993, supra). Ito et al. (1991, J. Clin. Invest. 87:1656–63) reported that A II caused a transient constriction of the isolated microperfused rabbit afferent arteriole and L-NNA augment A II-induced constriction, which suggest that the transient nature of A II-induced constriction may be due to enhanced NO synthesis. However, no direct data were provided and the observations of Ohishi et al. (1992, supra) in rat kidney arterioles did not support this idea in vitro.

Osteopontin

Osteopontin (OPN) is a secreted phosphoprotein having an apparent molecular weight of 44 kilo-Daltons (kDa) that is highly negatively charged and frequently associated with mineralization processes (Denhardt and Guo, 1993, FASEB J.). It is produced by many epithelial cell types and found both in normal plasma and in a variety of body secretions including urine, milk, and bile (Brown et al., 1992, Molec. Biol. Cell, 3:1169–80). Transformed cells, particularly ras-transformed cells, express OPN at elevated levels (Chambers et al., 1992, Anticancer Res. 12:43–48). Interaction of an Arg-Gly-Asp (RGD) sequence in OPN to an RGD-responsive integrin such as $\alpha_v\beta_3$, and its relatives $\alpha_v\beta_1$ and $\alpha_v\beta_5$, promotes cell adhesion and to activate a signal transduction pathway. One consequence of OPN signalling is an alteration in cellular $[Ca^{++}]_i$ levels; both a decrease (Miyanchi et al., 1991, J. Biol. Chem. 266:20369-74) and an increase (Zimolo et al., 1993, Amer. J. Physiol.) in osteoclasts have been observed. In the mouse kidney high level focal expression is observed in a subset of the nephrons, mostly in the epithelial cells of the thick ascending limb of the long loop of Henle, and in sclerosing glomeruli (Lopez et al., 1993, Lab. Invest.).

Osteopontin has been independently characterized as early T-cell activation protein 1 (ETA-1), bone sialoprotein I, 44 kDa-bone phosphoprotein, uroprotein, major transformation phosphoprotein, and activation protein-1 (Ap-1). Early studies demonstrated that rat osteopontin mediates cell binding via an RGD-site (Oldberg et al., 1986, Proc. Natl. Acad. Sci. U.S.A., 83:8819–23). Cantor et al. disclosed a protein homolog of rat osteopontin that was secreted by activated T lymphocytes and Thy-1-positive natural killer (NK) cells and functioned as a macrophage activator and chemattractant and an inducer of granulocyte/monocyte progenitor cell differentiation (U.S. Pat. No. 5,049,659, issued Sep. 17, 1991 to Cantor et al.)

Regulation of NO

Many proteins are reported to modulate NO production. Macrophage deactivating factor and TGF-β partially blocked NO release by macrophages activated with γIFN and TGFα, but not when activated by γIFN and lipopolysaccharide (LPS) (Ding et al., 1990, J. Immunol. 145:940–44). Epidermal growth factor can suppress both NO and $H_2O_2$ production by keratinocytes (Heck et al., 1992, J. Biol. Chem. 267:21277–80). Incubation of LPS-activated peritoneal neutrophils with IL-8 blocks both the release of NO and NOS induction at the transcriptional level (McCall et al., 1992, Biochem. Biophys. Res. Commun. 186:680–685). TGF-β1 and 12-O-tetradecanoylphorbol-13-acetate inhibit LPS and γIFN-induced NO synthesis in mouse bone marrow cells (Punjabi et al., 1992, J. Immunol., 148:2179–84). Both acidic and basic fibroblast growth factor inhibit (while TGF-β increases) nitrite production attributable to LPS plus γIFN treatment of bovine retinal pigmented epithelial cells, likely by inhibiting the induction of NOS mRNA at the transcriptional level (Goureau et al., 1993, Proc. Natl. Acad. Sci. U.S.A. 90:4276–80). Insulin-like growth factor I reduces the amount of NO produced by the action of IL-1β on vascular smooth muscle cells (Sehini et al., 1993, FASEB Expt. Biol. A243). The fact that so many agents can modulate NO activity by increasing or inhibiting NO production suggests that NO production may be important in many different contexts.

The citation of references herein shall not be construed as an admission that any such reference is prior art to the present invention.

SUMMARY OF THE INVENTION

The present invention is directed to a method for treating a disease or disorder involving an activity of nitric oxide (NO) in an animal subject. The method of the invention comprises administering a molecule to an animal subject suspected of having a disease or disorder involving an activity of nitric oxide in an amount effective to inhibit NO activity. The molecule is characterized by containing an epitope consisting of the epitope represented by the amino acid sequence arginine-glycine-aspartic acid (RGD), and has a molecular weight of at least about 300 Daltons. More particularly, the epitope is representated by the amino acid sequence glycine-arginine-glycine-aspartic acid-serine (GRGDS) (SEQ ID NO: 1). In a specific aspect of the invention, the molecule has a molecular weight of about 2145 Daltons. In another specific embodiment, the molecule has an apparent molecular weight by SDS-polyacrylamide gel electrophoresis of about 44,000 Daltons. More particularly, the molecule is a polypeptide.

In a specific embodiment, the molecule is a polypeptide that has about 20 amino acid residues, including a five-amino acid sequence glycine-arginine-glycine-aspartic acid-serine, such as the polypeptide having the amino acid sequence:

proline-threonine-valine-aspartic acid-valine-proline-aspartic acid-glycine-arginine-glycine-aspartic acid-serine-leucine-alanine-tyrosine-glycine-leucine-arginine-serine-leucine (SEQ ID NO: 2).

A particular advantage of the invention is the disclosure of a 20 amino acid polypeptide that is functionally active. Such relatively small molecules can be more readily administered, are easier to prepare, may be orally active, and can be more readily modified for increased half-life in vivo, increased activity, oral activity, and the like.

In another specific embodiment, the polypeptide is osteopontin. According to the invention, osteopontin may be administered to a subject. In another embodiment, a compound that induces in vivo expression of osteopontin is administered to a subject, in order to increase the level of natural osteopontin and thus inhibit NO activity. Compounds that induce osteopontin expression in one or more types of cell include but are not limited to interleukin-1 (IL-1), tumor growth factor-β (TGF-β), basic fibroblast growth factor (bFGF), calcitriol (vitamin $D_3$), progesterone, estrogen, dexamethasone, and activators of protein kinase C, such as phorbol esters.

The molecule of the invention can reduce the activity of inducible nitric oxide synthase (iNOS) and constitutive nitric oxide synthase (cNOS). More particularly, the molecule can suppress the induction of iNOS mRNA, and it can decrease the activity of the cNOS enzyme.

Specific diseases or disorders for which the therapeutic methods of the invention are beneficial include but are not limited to an inflammatory disease or disorder, hypotension, and the like. The inflammatory disease or disorder can be selected from the group consisting of but not limited to ischemia, septic shock, and cell mediated immune response. In specific embodiments, the inflammatory disease or disorder is mediated at least in part by a molecule selected from the group consisting of γ-interferon and lipopolysaccharide. In a specific aspect, the inflammatory disease or disorder is located in the inner ear or the kidney, however, the invention is not limited to therapy of these conditions exclusively.

As noted above, the present invention can be used in the treatment of hypotension, including but not limited to hypotension resulting from septic or traumatic shock, cronic hypotension, and disorders associated with hypotension, such as priapism. Accordingly, the invention further provides for administering an amount of a vasoconstrictor effective to increase blood pressure in an animal in addition to or in conjunction with administration of a molecule to inhibit production of NO. Suitable vasoconstrictors include, but are not limited to, epiniphrine; norepinephrine; vasopressin; $N^G$-monomethyl-L-arginine (L-NMA); $N^G$-nitroarginine methyl ester (L-NAME), the and the prostaglandins $PGE_1$ and $PGF_1$.

In a specific aspect, the invention provides a method for inhibiting smooth muscle cell relaxation in response to nitric oxide comprising administering an amount of a molecule effective to inhibit nitric oxide production to an animal subject suspected of having a need for such treatment, which molecule is characterized by containing an epitope consisting of the epitope represented by the amino acid sequence arginine-glycine-aspartic acid (RGD), and which molecule has a molecular weight of at least about 300 Daltons. More particularly, the epitope is represented by the amino acid sequence glycine-arginine-glycine-aspartic acid-serine (GRGDS) (SEQ ID NO: 1).

In a specific example, infra, the invention provides for administration of the molecule to affect kidney proximal tubule epithelial cell function.

In addition to the methods of the invention, the invention further provides a molecule effective to inhibit nitric oxide production, which molecule is characterized by containing an epitope consisting of the epitope represented by the amino acid sequence arginine-glycine-aspartic acid (RGD), and which molecule has a molecular weight of at least about 300 Daltons and not greater than about 10,000 Daltons, preferably not greater than about 5000 Daltons, and more preferably not greater than about 2500 Daltons; and a pharmaceutically acceptable carrier. More particularly, the molecule can be a polypeptide, e.g., a polypeptide having about 20 amino acid residues, including a five-amino acid sequence glycine-arginine-glycine-aspartic acid-serine (SEQ ID NO: 1). In a specific embodiment, the polypeptide has an amino acid sequence as follows:

proline-threonine-valine-aspartic acid-valine-proline-aspartic acid-glycine-arginine-glycine-aspartic acid-serine-leucine-alanine-tyrosine-glycine-leucine-arginine-serine-leucine (SEQ ID NO: 2).

According to the invention, the peptide can be protected or derivitized in various ways, e.g., N-terminal acylation; C-terminal amidation; cyclization; etc. In a specific embodiment, the N-terminus of the peptide is acetylated.

The invention further provides pharmaceutical compositions comprising such molecules.

In yet a further embodiment of the invention, the pharmaceutical composition also comprises a vasoconstrictor effective to increase blood pressure in an animal.

The present invention also provides, in an additional aspect, a method for decreasing blood pressure in an individual in need of such treatment. The method comprises administering to a subject an amount of an inhibitor of osteopontin activity effective to inhibit osteopontin activity. In a specific embodiment, the inhibitor can inhibit expression of osteopontin. In another embodiment, the inhibitor can competitively or non-competitively inhibit osteopontin. Competitive inhibitors of osteopontin include but are not limited to RGD-containing peptides and proteins and antibodies to integrins. Non-competitive inhibitors of osteopontin include but are not limited to antibodies specific for osteopontin.

It is a primary object of the present invention to provide methods for treating diseases or disorders associated with production of nitric oxide.

Thus, it is an object of the present invention to provide compositions and methods for inhibiting production of nitric oxide, whether by inducible nitric oxide synthase or constitutive nitric oxide synthase.

It is a further object of the invention to provide a small molecule, e.g., of approximately 500–10,000 Daltons molecular weight, that inhibits production of NO.

Yet another object of the invention is to provide structural information about functionally active osteopontin and fragments thereof for use in the rational design of molecules of the invention.

It is yet another object of the invention to provide an orally effective molecule for inhibiting NO production and activity.

These and other objects of the present invention can be readily appreciated by reference to the following drawings and Detailed Description of the Invention.

DETAILED DESCRIPTION OF THE INVENTION

Figure 1:
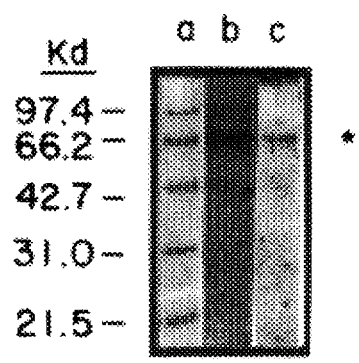
FIG. 1. SDS-page and Western blot analysis of purified OPN. Approximately 5 µg of purified OPN was electrophoresed in two lanes (b, c) of a 12% polyacrylamide-SDS gel, each of which was blotted onto nitrocellulose. The lanes are: a) protein markers, stained with Commassie blue; b) total protein stained with ISS Pro-Blue™ and Silver Stain-Daichi (Integrated Separation Systems, Natick, Mass.). The black and white photograph does not do justice to the silver-stained gel, which showed a very intense blue-green color at the position of OPN (indicated by the asterisk), suggesting that the purity was even better than evident here; and, c) protein immunoreactive with the polyclonal anti-OPN antiserum LF-7 detected with anti-rabbit IgG (BioRad) conjugated to horseradish peroxidase and visualized with enhanced chemiluminescence (ECL, Amersham, Chicago, Ill.). OPN does not stain well with Coomassie blue.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984).

Therefore, if appearing herein, the following terms shall have the definitions set out below.

According to the invention, the term "molecule" refers to a polypeptide, or a derivative or analog thereof, as these terms are defined hereinafter, having an activity including the ability to inhibit production of nitric oxide and containing an epitope found on osteopontin, which epitope contains an amino acid sequence consisting of arginine-glycine-aspartic acid. In particular, the term "molecule" encompasses peptidomimetics, i.e., molecules having some structural and functional characteristic in common with peptides, but that do not contain peptide bonds. In a specific embodiment, the molecule is osteopontin. In another embodiment, the molecule is a 20-amino acid fragment of osteopontin.

As used herein, the term "functionally active" refers specifically to the ability to inhibit an activity of nitric oxide. More particularly, the term includes one or more of inhibition of production of nitric oxide, suppression of the activity of inducible NO synthase, suppression of the activity of constitutive NO synthase, and inhibition of expression of an NO synthase.

An "activity of nitric oxide" includes, but is not limited to, vasodilation, hypotension, cytotoxicity, contribution to septic shock, ischemic injury (hypoxic injury), reduction in intracellular calcium levels, reduction of intracellular oxidants, and the like, such as are described in the Background of the Invention section, supra.

An "epitope" refers generally to a specific recognition feature of a molecule, which depends on the topological orientation of functional groups of the molecule. According to the invention, a molecule contains an epitope, or shares an epitope, of a second molecule if the first molecule specifically binds or interacts competitively with specific binding of the second molecule. There is no requirement that shared epitopes be chemically identical; however, shared epitopes must be topologically similar, i.e., have a topological arrangement of chemical functional groups that is similar in each molecule, in order to interact competitively with a target molecule. "Target molecules" include, but are not limited to, cell surface receptors, antibodies, and the like.

"Osteopontin" refers to the secreted phosphoprotein having an apparent molecular weight of 44 kDa that is highly negatively charged and frequently associated with mineralization processes, and that contains the amino acid sequence Arg-Gly-Asp (RGD). As used herein, osteopontin includes, but need not be limited to, the proteins described in Oldberg et al., 1986, Proc. Natl. Acad. Sci. U.S.A. 83:8819–23; Craig et al., 1989, J. Biol. Chem. 264:9682–89; Cantor et al., U.S. Pat. No. 5,049,659, issued Sep. 17, 1991, each of which is specifically incorporated herein by reference, as well as to homologous proteins from other species.

A composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin. "Chemical synthesis" refers to synthesis conducted in vitro using well defined organic chemical reactions and purified reagents. Thus, chemical synthesis is distinct from biological synthesis, which involves cellular biological machinery.

Various abbreviations are used throughout the specification, including: A II, angiotensin (the x-mer peptide produced from angiotensinogen); FGF, fibroblast growth factor; IFN, interferon; IL, interleukin; kDA, kilo-Daltons; L-NAME, L-$N^G$-nitroarginine methyl ester; L-NMA, $N^G$-methyl-L-arginine; LPS, lipopolysaccharide; NOS, nitric oxide synthase (iNOS, inducible NOS; cNOS, constitutive NOS); OPN, osteopontin; PTE, proximal tubule epithelial; TNF, tumor necrosis factor; TGF, tumor growth factor; OPP, osteopontin peptide having the sequence PTVDVPDGRGDSLAYRLRSK (SEQ ID NO: 2). Standard three-letter and one-letter abbreviations for the 20 common amino acids are used throughout the specification (see, Stryer, 1981, *Biochemistry*, W. H. Freeman and Company: San Francisco, p. 16).

In its primary aspect, the invention relates to the use of a molecule, in particular, osteopontin, or fragments, derivatives or analogs thereof, to inhibit NO production, and thereby regulate the effects of NO in vivo. The ability of osteopontin, and fragments, derivatives or analogs thereof, to inhibit NO production is an unknown function of such molecules.

Thus, the present invention relates to fragments, derivatives and analogs of osteopontin, as well as to osteopontin itself. According to the invention, as described in detail infra, the functional molecule can be obtained from any source, e.g., by purification from natural sources; using recombinant DNA technology; or by chemical synthesis.

The present invention further relates to the unique compounds that have the described functional and structural properties, and to pharmaceutical compositions comprising these compounds.

Inhibition of NO production has many important therapeutic benefits, as described infra. NO production contributes to septic shock, the adverse consequences of ischemia, inflammation, hypotension, development, cell death and other physiological processes and effects. The cytokines IL-2 and TNF, which have significant potential as chemotherapeutic agents to treat cancer, induce high levels of NO production, resulting in hpotensive shock. The present invention contemplates reversing this adverse side effect by administering NO inhibitors with these cytokines. Thus, the functional molecules of the invention may be useful as primary or ancillary therapeutic agents for the treatment of these and other NO-mediated diseases or disorders, or effects.

The present invention is based, in part, on the observation that osteopontin (OPN), a secreted, Arg-Gly-Asp-containing phosphoprotein expressed at high levels in the kidney, suppresses nitric oxide (NO) synthesis. In one aspect of the invention, osteopontin inhibits the activity of induced NO synthase (iNOS); in another aspect of the invention, NO inhibits the activity of constitutive NO synthase (cNOS).

In a specific embodiment, NO inhibits iNOS induced by the inflammatory mediators γ-interferon (γ-IFN) and lipopolysaccharide (LPS) in primary mouse kidney proximal tubule epithelial cells. Northern blot and immunofluorescence analyses of inducible nitric oxide synthase (iNOS) expression revealed that the inflammatory mediators increased iNOS mRNA and protein levels. Recombinant human OPN (purified from both mammalian cells or produced by recombinant *E. coli* cells) inhibited this response by a process that was blocked by anti-OPN antiserum and by the peptide GRGDS (SEQ ID NO: 1), but not GRGES (SEQ ID NO: 3).

The invention is further partly based on the observation that a 20-amino acid residue fragment of osteopontin that contains the GRGDS sequences could also inhibit the γ-IFN and LPS-induced response.

Although not intending to be limited to any particular theory, these data suggest that inhibition of NO synthesis by OPN in kidney cells is mediated by an integrin, possibly the $α_v β_3$ integrin, which is known to be an OPN receptor. NO is believed to control blood flow through the glomerulus, regulating salt and water balance, and to be important as a defense against tumor cells and infecting microorganisms. The experimentally observed ability of OPN to inhibit the induction of iNOS and activity of cNOS suggests that OPN may be an important regulator of the NO signalling pathway and NO-mediated cytotoxic processes.

Source of Molecules

According to the present invention, osteopontin, or fragments, derivatives and analogs thereof, can be obtained from any source. Production of derivatives and analogs is more fully disclosed infra.

For example, osteopontin can be purified from natural sources, as described in the references cited above, in particular in the Background of the Invention section of the application.

In another embodiment, a gene encoding osteopontin can be expressed using well known techniques of recombinant molecular biology (see, e.g., Sambrook et al., 1990, and the other references cited supra). In specific embodiments, osteopontin is expressed in a recombinant fusion protein in human embryonic kidney cell lines and in *Escherichia coil* bacteria, and purified.

For example, human OPN cDNA can be cleaved with appropriate restriction endonucleases and inserted in to an appropriate expression vector using appropriate linkers. In a specific example, the expression vector is pNMH. The plasmid is then introduced into host cells for expression. In a specific embodiment, the plasmid is linearized and introduced into MH2 (human embryonic kidney) cells, e.g., via a calcium phosphate-DNA mediated transfection procedure. After selection, e.g., by antibiotic resistance, expression clones are selected. Selection can be determined by one or more of Southern, Northern, and Western analysis; by assays for osteopontin activity; or by any means known in the art.

Yield of osteopontin can be enhanced by controlling expression with a constitutive or an inducible promoter. Expressed osteopontin can be obtained from culture medium of mammalian host cells, or from the cytosol of *E. coli*. In one embodiment, the expressed protein is purified from culture medium. In order to simplify the purification process, serum free medium is preferably used with mammalian host cells. Osteopontin can be purified using ion exchange chromatography, e.g., on a DEAE-SEPHAROSE column, by gel filtration chromatography, e.g., on a SEPHAROSE G-100 column, or by a combination of procedures. In another embodiment, purification from *E. coli* host cells involves ammonium sulfate precipitation, hydroxyapatite chromatography, and SDS-gel electrophoresis. Refolding of recombinantly produced osteopontin, from either eucaryotic or procaryotic expression systems, has not been found to be necessary.

In various assays, it has been found that recombinant osteopontin from bacterial expression systems, in particular *E. coli*, has activities similar to those detected for the protein made in mammalian cells, depsite the fact that the protein derived from expression in bacterial host cells lacks post-translational modifications, such as glycosylation, that are believed to be characteristic of the protein made in eukaryotic cells.

In yet another embodiment, osteopontin or fragments thereof can be prepared using chemical peptide synthesis. Techniques for chemical peptide synthesis are well known in the art. For example, see Fields and Noble, 1990, "Solid phase peptide synthesis utilizing 9-fluorenylmethoxycarbonyl amino acids", Int. J. Pept. Protein Res. 35:161–214; Stewart and Young, 1984, Solid Phase Synthesis, Second Edition, Pierce Chemical Co., Rockford, Ill. In a specific embodiment, infra, a 20-amino acid fragment of osteopontin was chemically synthesized.

Structure of the Molecule

The structure of osteopontin and functionally active fragments thereof can be analyzed by various methods known in the art to determine the topology of the RGD epitope. Once the structure of osteopontin and its functionally active fragments is determined, rational design of analogs of osteopontin can proceed more exactly.

It is a particular advantage of the present invention that a functionally active fragment of osteopontin is provided. In a specific embodiment, the fragment is the 20-amino acid fragment described above and in Example 1. Structural analysis proceeds more readily with small molecules than large ones, as smaller molecules are less complex. Furthermore, hypotheses with respect to structure can be tested more easily because manipulation of a smaller molecule can be accomplished and evaluated more readily than with a large one.

The osteopontin protein sequence can be characterized by a hydrophilicity analysis (Hopp, T. and Woods, K., 1981, Proc. Natl. Acad. Sci. U.S.A. 78:3824). A hydrophilicity profile can be used to identify the hydrophobic and hydrophilic regions of the protein.

Secondary structural analysis (Chou, P. and Fasman, G., 1974, Biochemistry 13:222) can also be done, to identify regions of osteopontin that assume specific secondary structures.

Manipulation, translation, and secondary structure prediction, as well as open reading frame prediction and plotting, can also be accomplished using computer software programs available in the art.

Other techniques for determining structure include, but are not limited to, nuclear magnetic resonance (NMR), infrared (IR), Raman, and ultraviolet (UV), especially circular dichroism (CD), spectroscopic analysis. In particular, NMR provides very powerful structural analysis of molecules in solution, which more closely approximates their native environment (Marion et al., 1983, Biochem. Biophys. Res. Comm. 113:967–974; Bar et al., 1985, J. Magn. Reson. 65:355–360; Kimura et al., 1980, Proc. Natl. Acad. Sci. U.S.A. 77:1681–1685). Other methods of structural analysis can also be employed, including but not limited to X-ray crystallography (Engstom, A., 1974, Biochem. Exp. Biol. 11:7–13). Computer modeling can also be used, especially in connection with NMR or X-ray methods (Fletterick, R. and Zoller, M. (eds.), 1986, Computer Graphics and Molecular Modeling, in *Current Communications in Molecular Biology*, Cold Spring Harbor Laboratory, Cold Spring Harbor, N.Y.).

Osteopontin Derivatives and Analogs

The invention further relates to molecules that are functionally active derivatives and analogs of osteopontin or fragments thereof. According to the invention, such functionally active derivatives or analogs of osteopontin or fragments thereof contain an epitope consisting of the epitope represented by a peptide that has the amino acid sequence arginine-glycine-aspartic acid.

The production and use of derivatives and analogs related to osteopontin are within the scope of the present invention. The derivative or analog is functionally active, i.e., capable of inhibiting nitric oxide activity, and more particularly, NO production, as is characteristic of full-length, wild-type osteopontin. Derivatives or analogs of osteopontin can be tested for the desired activity by procedures known in the art, including but not limited to the assays described in the Examples.

In particular, derivatives can be made by altering osteopontin encoding nucleic acid sequences by substitutions, additions or deletions that provide for functionally equivalent molecules. Due to the degeneracy of nucleotide coding sequences, other DNA sequences which encode substantially the same amino acid sequence as an osteopontin gene may be used in the practice of the present invention. These include but are not limited to nucleotide sequences comprising all or potions of osteopontin genes, which are altered by the substitution of different codons that encode the same amino acid residue within the sequence, thus producing a silent change. Likewise, the derivatives of the invention include, but are not limited to, those containing, as a primary amino acid sequence, all or part of the amino acid sequence of a osteopontin protein including altered sequences in which functionally equivalent amino acid residues are substituted for residues within the sequence resulting in a conservative amino acid substitution.

In a specific embodiment, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Derivatives or analogs include but are not limited to those peptides which are substantially homologous to osteopontin or fragments thereof, or whose encoding nucleic acid is capable of hybridizing to a osteopontin nucleic acid.

The derivatives and analogs of the invention can be produced by various methods known in the art. The manipulations which result in their production can occur at the gene or protein level.

For example, the osteopontin gene sequence can be modified by any of numerous strategies known in the art (Sambrook et al., 1990, supra). The sequence can be cleaved at appropriate sites with restriction endonuclease(s), followed by further enzymatic modification if desired, isolated, and ligated in vitro. In the production of the gene encoding a derivative or analog of osteopontin, care should be taken to ensure that the modified gene remains within the same translational reading frame as osteopontin, uninterrupted by translational stop signals, in the gene region where the desired osteopontin functional activity is encoded.

Additionally, the osteopontin-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

Manipulations of the osteopontin or fragments thereof may also be made at the protein level. Included within the scope of the invention are derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, conjugation to polyethylene glycol (PEGylation), etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Alternatively, the derivatives or analogs of the invention can be prepared synthetically. Preferably, the synthetic analog contains chemical functional groups in a correct topology so that the analog molecule contains the RGD epitope of osteopontin and demonstrates appropriate functional activity of osteopontin. The correct topology can be determined from the structural analysis of osteopontin, or more preferably, a functionally active fragment of osteopontin such as the 20-amino acid fragment disclosed herein.

According to the invention, an analog can refer to a molecule containing subunit amino acids or amino acid analogs. In particular, the term analog refers to peptidomimetics. The subunits may be linked by peptide bonds. In another embodiment, the subunit(s) may be linked by other bonds, e.g., ester, ether, etc. As used herein the term "amino acid" refers to natural amino acids, including glycine, unnatural or synthetic amino acids, both the D or L optical isomers of amino acids, and amino acid analogs, including mimics of di-, tri-, and larger peptides.

In a further embodiment, subunits of "peptides" that confer useful chemical and structural properties on the molecule in which such peptides are incorporated can be chosen. For example, peptides comprising D-amino acids will be resistant to L-amino acid-specific proteases in vivo. In addition, the present invention envisions preparing peptides that have more well defined structural properties, and the use of peptidomimetics, and peptidomimetic bonds, such as ester bonds, to prepare peptides with novel properties.

In another embodiment, a peptide may be synthesized that incorporates a reduced peptide bond, i.e., $R_1$—$CH_2$—$NH$—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would demonstrate unique function and activity, such as extended half-lives in vivo due to resistance to metabolic breakdown or endogenous protease activity. Furthermore, it is well known that in certain systems constrained peptides show enhanced functional activity (Hruby, 1982, Life Sciences 31:189–199; Hruby et al., 1990, Biochem J. 268:249–262); the present invention contemplates use of constrained peptides.

Therapeutic Methods

According to the present invention, the ability to inhibit NO production has many important therapeutic benefits. Nitric oxide activity can be associated with inflammation, septic shock, adverse consequences of ischemia and reperfusion injury, hypotension, and cell development and cell death, to mention a few indications.

Inflammation involves cell mediated immune response, with release of toxic molecules including NO. Of particular importance in the inflammatory response are macrophages, and the invention is particularly directed to inhibiting NO production by these cells. Cell mediated immune response can be beneficial, e.g., for destroying infectious microorganisms such as bacteria and parasites, and for eliminating cancerous or virally infected cells. However, inflammation can become chronic, autoimmune, and detrimental. Therefore, the methods and compositions of the invention can be useful for treating inflammation, for example, lung inflammation, such as asthma; liver inflammation; inflammatory bowel disease, which presently is uncurable; arthritis; and the like. NO activity inhibitory molecules of the invention can be administered either as a primary therapy or in conjunction with other anti-inflammatory therapies, such as, but not limited to, steroid treatment, immune-cell targeted antibody therapy, and the like.

Septic shock results from the host response to systemic bacterial infection, particularly to bacterial endotoxins, such as Gram negative lipopolysaccharides. Nitric oxide overproduction contributes to septic shock. Any reduction in NO production will have an ameliorating effect on the symptoms of septic shock. The invention thus provides for administration of osteopontin, or a fragment, derivative or analog thereof, for the treatment of septic shock, whether as a primary therapy or in conjunction with other therapies, e.g., antibodies to lipopolysaccharide, antibodies to tumor necrosis factor or interleukin 1, or soluble TNF or IL-1 receptors. Macrophages are a particular cellular target for inhibition of NO activity. To date, septic shock in humans has proved to be highly refractory to therapy. Therefore, it is a particular advantage of the invention to provide a therapy or co-therapy for septic shock.

NO has been associated with the adverse effects of ischemic events. Ischemia, or hypoxia, is a particularly serious problem when it occurs in the heart, e.g., as a consequence of myocardial infarct or after balloon angioplasty; in the brain, e.g., as a consequence of stroke; and in the kidneys. Therefore, administration of a molecule of the invention would greatly benefit a subject suspected of suffering from ischemia or reperfusion injury. Preferably, the NO inhibitory molecule is administered prior to or concomitant with any drugs designed to release the blockage causing the ischemic condition. In a specific embodiment, osteopontin, or a fragment, derivative or analog thereof is administered prior to or with tissue plasminogen activator (tPA), streptokinase, APSAC, and the like for treating myocardial infarct.

Hypotension, or low blood pressure, can cause problems with circulation. Hypotension, and shock, can result from spetic shock, severe blood loss, serious organ injury, severe trauma and chemotherapy, particularly cytokine-based chemotherapy. Thus, the present invention provides for treatment of severe hypotension. In a specific embodiment, priapism (impotence) associated with hypotension can be treated. In another specific embodiment, hypotensive shock that may result from administration of IL-2 or TNF to treat cancer can be ameliorated.

NO is an active neurotransmitter. Excessive production or activity of NO may result in neurological diseases, particularly those affecting the brain. Therefore, administration of a molecule of the invention, i.e., osteopontin, or a fragment, derivative or analog thereof, can be beneficial for the treatment of neurological diseases or disorders. In a preferred aspect, the molecule is an analog of osteopontin that can cross the blood brain barrier, which would allow for intravenous or oral administration. Many strategies are available for crossing the blood brain barrier, including but not limited to, increasing the hydrophobic nature of a molecule; introducing the molecule as a conjugate to a carrier, such as transferrin, targeted to a receptor in the blood brain barrier; and the like. In another embodiment, the molecule can be administered intracranially or, more preferably, intraventricularly.

The NO activity inhibitory molecules of the invention can also be used to modulate downstream events mediated by NO-induced reduction in the levels of intracellular calcium and in the levels of intracellular oxidants. Thus, the methods of the invention can be used to modulate development, cell death, and the like. The invention further provides for intervention in direct NO-mediated killing, which is important in neuronal cell death.

In a further embodiment, the methods and compositions of the invention are useful in the therapeutic treatment of diseases or disorders of the kidney. Glomerulonephritis is characterized by enhanced production of NO, which may contribute to tissue injury. During inflammation or reperfusion, or other stress related processes, kidney cells are exposed to an array of factors and mediators that can stimulate excessive NO production. Excessive NO production results in increases in reactive intermediates, which can damage kidney tissues. Enhanced NO production is also a serious consequence of uremia. Thus, the present invention provides for the amelioration or alleviation of many diseases of the kidney.

Certain metastatic diseases can also be treated by administration of osteopontin, according to the present invention. For example, inhibition of NO activity, which can result in reduced blood flow, may aid in a treatment of solid tumors that involves or is enhanced by hypoxia.

The therapeutic methods and compositions of the invention may also be useful for the treatment of altitude sickness.

Altitude sickness is thought to result from reduced oxygen tension and consequential hypoxia of certain tissues, particularly the lungs and brain. According to the present invention, administration of osteopontin, or a fragment, derivative or analog thereof, may alleviate the symptoms of altitude sickness.

In a further embodiment, diseases or disorders associated with NO can be treated by administering a substance that induces osteopontin expression rather than by directly administering osteopontin.

According to the present invention, in cases of high blood pressure reduction of osteopontin expression can benefit a patient. Decreasing the level of osteopontin, e.g., by administration of an inhibitor of osteopontin expression or by administering an agent that competitively or non-competitively inhibits osteopontin activity, allows increased production of NO, resulting in vasodilation and a decrease in blood pressure. As is demonstrated in a specific example, infra, a peptide having the amino acid sequence GRGDS (SEQ ID NO: 1) can competitively inhibit osteopontin activity, thus allowing for greater NO production. Other inhibitors of osteopontin include, but are not limited to, an anti-osteopontin antibody; other molecules that bind to $\alpha_v\beta_3$ and analogous integrins; antibodies that bind to integrins and competitively inhibit binding of natural ligands; and RGD-containing peptides and proteins that competelively bind to integrins.

The effective dose of a molecule of the invention, and the appropriate treatment regime, can vary with the indication and patient condition, and the nature of the molecule itself, e.g., its in vivo half life and level of activity. These parameters are readily addressed by one of ordinary skill in the art and can be determined by routine experimentation.

A pharmaceutical composition of the invention contains an appropriate pharmaceutically acceptable carrier as defined supra. These compositions can take the form of solutions, suspensions, tablets, pills, capsules, powders, sustained-release formulations and the like. Suitable pharmaceutical carriers are described in Remington's Pharmaceutical Sciences by E. W. Martin. The NO activity inhibitory molecules of the invention can be administered in liposomes (see Langer, 1990, Science 249:1527–1533; Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally Liposomes in the Therapy of Infectious Disease and Cancer, supra). Such compositions will contain an effective therapeutic amount of the active compound together with a suitable amount of carrier so as to provide the form for proper administration to the subject.

While intravenous injection is a very effective form of parenteral administration, other modes can be employed, including but not limited to intraventricular, intramuscular, intraperitoneal, intra-arteriolar, and subcutaneous injection as well as oral, nasal and topical administration.

The therapeutic agents of the instant invention may be used for the treatment of animal subjects or patients, and more preferably, mammals, including humans, as well as mammals such as dogs, cats, horses, cows, pigs, guinea pigs, mice and The invention will be further clarified by the following examples, which are intended to be purely exemplary of the invention.

EXAMPLE 1

The present example demonstrates that osteopontin inhibits induction of nitric oxide synthase gene expression by inflammatory mediators in mouse kidney epithelial cells. In particular, osteopontin and a 20-amino acid fragment of osteopontin that contains the RGD sequence both suppress nitric oxide (NO) synthesis induced by inflammatory mediators in primary mouse kidney proximal tubule epithelial cells. The ability of osteopontin and a fragment of osteopontin that contains the GRGDS sequence to inhibit production of inducible NO-synthase (iNOS) has important implications for the prevention of NO-mediated damage during inflammatory responses.

Experimental Procedures

Cell culture. Primary proximal tubule epithelial (PTE) cells were prepared from the kidneys of 6–8 week old CD1 mice using culture conditions shown to be selective for tubule epithelial cells (Markewitz et al., 1993, J. Clin. Invest. 91:2138–43). Briefly, slices of cortex from decapsulated kidneys were washed in unsupplemented RPMI 1640 and cut int 1–2 mm³ pieces, which were then incubated for 20 min. at 37° C. in Krebs-Henseleit buffer (Sigma Chemical Co., St. Louis, Mo.) supplemented with 10 mM HEPES (pH 7.5), 1 g/l D-glucose, 200 mg/1 sodium pyruvate, 0.125 mg/ml collagenase (Type 1A, Sigma), and 0.6 U/ml dispase (Boehringer Mannheim Biochemica, Indianapolis, Ind.). The digested cortex was centrifuged at 70×g for 3 min and the cells resuspended in RPMI 1640 supplemented with 10 mM HEPES (pH 7.5), 5 µg/ml human transferrin, 50 nM dexamethasone, 5 µg/ml insulin (Gibco, Gaithersberg, Md.), 3% fetal bovine serum, 100 U/ml penicillin and 100 µg/ml streptomycin.

For NO measurements, cells were subcultured into 24-well culture plates (Linbro, Hamden, Conn.) at $5\times10^4$ cells/16-mm well and incubated overnight. After removal of the medium, the cells were washed 3 times with Dulbecco's phosphate buffered saline (Sigma D5652), and re-fed with phenol red-free RPMI 1640 medium containing 2 mM l-arginine and 10 µg/ml tetrahydrobiopterin (ICN Biochemicals, Cleveland, Ohio) in the presence or absence of 100 ng/ml lipopolysaccharide (LPS) (Sigma) and 100 U/ml recombinant mouse γ-interferon (γ-IFN).

$N^G$-methyl-L-arginine (L-NMA) was obtained from BIOMOL Research Laboratory Inc. (Plymouth Meeting, Pa.).

Northern blot analysis. Total RNA was isolated using the TRI reagent (Molecular Research Center, Cincinnati, Ohio). The RNA (5 µg) was fractionated on formaldehyde-agarose gels, blotted and probed using standard procedures (Sambrook et al., 1989, supra). The mouse cDNA corresponding to the macrophage inducible nitric oxide synthase gene (iNOS) has been described (Lyons, 1992, J. Biol. Chem. 267:6370–74).

Measurement of NO (as $NO_2^-$) production. Nitric oxide is a short-lived reactive nitrogen intermediate that in aqueous solution in the absence of oxyhemoproteins or superoxide, is oxidized primarily to nitrite (Ignarro et al., 1993, Proc. Natl. Acad. Sci. U.S.A. 90:8103–07). Under such conditions NO production can be assessed by the accumulation of nitrite in the medium. Nitrite was detected using the Griess reagent, which is generated by mixing equal volumes of 60 mM sulfanilamide in 50% $H_3PO_4$ and 4 mM N-1-naphthylethylenediamine dihydrochloride in $H_2O$. Incubation of 1 vol of medium first with 1 vol sulfanilamide then 5 min later with 1 vol N-1-naphthylethylenediamine dihydrochloride results in the formation of a purple azo dye, indicative of the presence of nitrite, that can be qualified spectrophotometrically after 30 min at 540 nm (Green et al., 1982, Anal. Biochem. 126:131–138).

Preparation of OPN proteins and peptides. A human OPN cDNA (Young et al., 1990, Genomics 7:491–502) was cleaved with XbaI and XhoI from a pBLUESCRIPTc SK± vector. The cleaved insert was cloned into the BamH1 site of the mammalian expression vector pNMH under the control of the mouse metallothionein-1 promoter (Khokha and Denhardt, 1987, Anticancer Res. 7:653–660) by using BamH1 linkers. The OPN-producing plasmid, designated pNMH.OPN, was linearized and transfected into MH2 cells by a calcium phosphate-DNA mediated transfection procedure. (MH2 is a cell line obtained from human embryonic kidney cells by immortalization with the Ad12E1a gene; this line does not express endogenous OPN.) Forty-six hours after transfection, cells from each dish were replated and selected for neo$^r$ in the presence of 200 µg/ml active G418 (antibiotic). After 2½ weeks of neo$^r$ selection, clones were picked from each transfectant and were analyzed by Southern, Northern and Western blots. From the resulting G418$^r$ clones, one was isolated that had multiple copies of the expression cassette integrated into the chromosome and could be induced with 0.5 µM $Cd^{2+}$ to express high levels of OPN.

OPN was purified from serum-free, $Cd^{2+}$-containing αMEM conditioned by cells for 18–20 h. Culture medium was passed directly onto a DEAE-SEPHAROSE FAST Flow column that had been equilibrated with 0.05M Tris-HCl, pH 7.5. The column was washed with two column volumes of starting buffer and bound proteins were eluted with a linear gradient (0.2 to 0.6M NaCl). The eluted proteins from each fraction were monitored by absorbance at 280 nm. Fractions were pooled according to peak absorbance, dialyzed against water, and lyophilized. Each pool was analyzed on 12% SDS-PAGE and blotted onto a nitrocellulose membrane. The blotted proteins were probed with LF-7, an anti-human OPN antibody. The fractions containing OPN were subjected to gel filtration on a SEPHAROSE G-100 column, equilibrated with 0.01 M Tris-HCl, pH 7.5. Fractions were pooled according to peak absorbance, dialyzed against water, freeze dried, and analyzed by western blotting.

FIG. 1 illustrates the quality and purity of the OPN preparation used in this work. Protein concentrations were determined with the Pierce bicinchoninic acid reagent. GST-OPN is a fusion protein of human osteopontin with glutathione-S-transferase purified from *E. coli* (Xuan et al., 1993, "Recombinant GST-human osteopontin fusion protein is functional in RGD-dependent cell adhesion", J. Cell. biochem. 55:1–9).

OPP is the peptide Ac-Pro-Thr-Val-Asp-Val-Pro-Asp-Gly-Arg-Gly-Asp-Ser-Leu-Ala-Tyr-Gly-Leu-Arg-Ser-Lys-$NH_2$ (SEQ ID NO: 2) and was synthesized by American Peptide Company, Inc., Sunnyvale, Calif.; it represents a sequence around the consensus ArgGlyAsp (RGD) sequence in OPN.

Results

Figure 2:
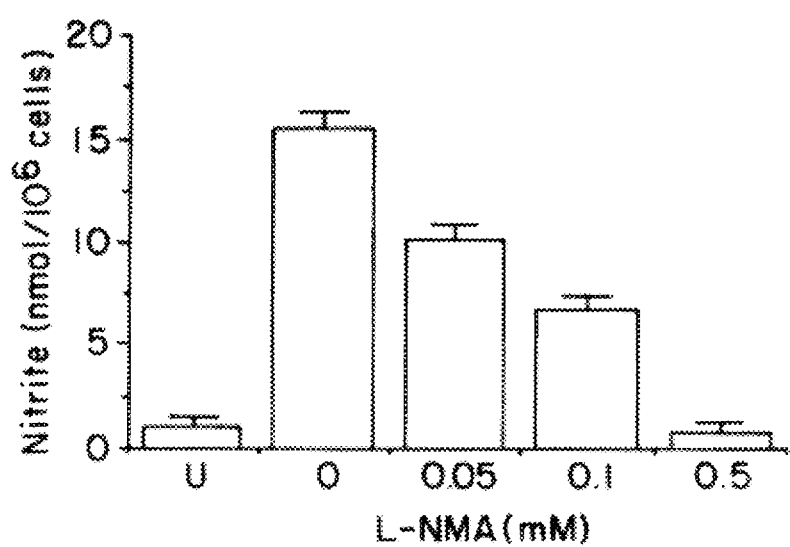
FIG. 2. The arginine analog L-NMA inhibits production of nitrite by primary tubule epithelial cells. Cells were cultured and stimulated with LPS and γIFN. L-NMA was added simultaneously with the inducing agents in fresh medium at the indicated concentration. U: unstimulated cells, no L-NMA. Nitrite in the medium was measured at 24 h. The values are the mean±standard error from three separate plates.
Figure 3A:
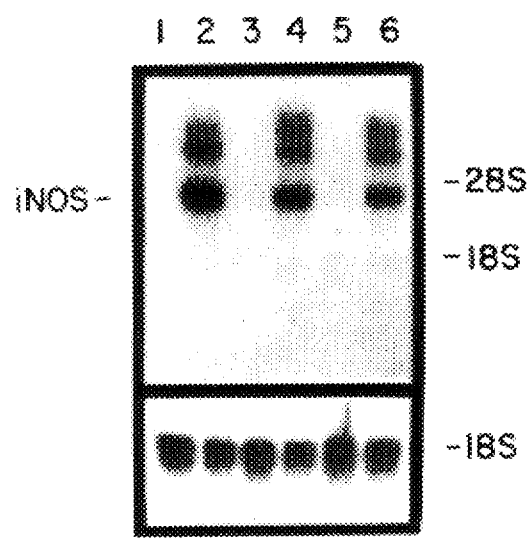
FIGS. 3A and 3B. Inhibition of inducible NO-synthase (iNOS) gene induction by OPN. A) Northern blot analysis of iNOS mRNA and 18s rRNA levels in primary mouse kidney epithelial cells 8 h after treatment. B) Accumulation of nitrite in the medium 24 h after treatment. Values are the mean±standard error from three separate plates. Lane 1: control; lanes 2, 4 and 5: stimulated with 100 ng/ml LPS plus 100 U/ml γIFN; lanes 3 and 4: treated with 1 pM OPN; lanes 5 and 6: treated with 100 pM OPN.

Generation of NO by tubule epithelial cells. Cultures of primary mouse kidney epithelial cells accumulated nitrite in the medium in a time-and dose-dependent manner when stimulated with LSP and γINF, or γIFN alone, but not when not stimulated or stimulated with LPS alone (data not shown, but see below). Inhibition of nitrite accumulation by the arginine analog $N^G$-methyl-L-arginine (L-NMA) (FIG. 2) strongly suggests that nitrite synthesis is dependent upon a nitric oxide synthase. Confirmation that the nitrite is indeed indicative of NO synthesis was provided by the fact that stimulated cells had substantially enhanced level of the mRNA encoding the inducible nitric oxide synthase (iNOS) (FIG. 3A, lane 2). An immunofluorescence analysis revealed increased amounts of iNOS protein, largely in a perinuclear location, in essentially all of the stimulated cells (FIG. 4). The experiments establish that inflammatory mediators induce NO synthesis in these cells by increasing expression of the iNOS gene.

Figure 3B:
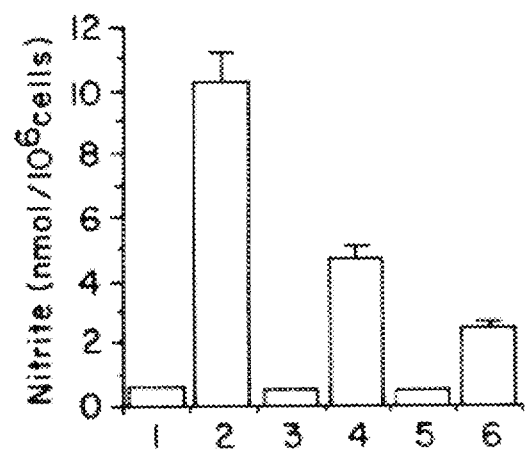
Figure 4A:
FIGS. 4A–D. OPN-induced suppression of iNOS protein in PTE cells. Cells were fixed and permeabilized by incubation of 30 min with 0.4 mM lysophosphatidylcholine in 1% buffered formalin. After washing three times with phosphate-buffered saline, cells were blocked with 0.1% bovine serum albumin in phosphate-buffered saline and then incubated for 4 h first with a 1:10,000 dilution of rabbit peptide antibody to the C-terminal 10 amino acids of iNOS. After washing, the cells were incubated with FITC-conjugated goat-anti rabbit secondary antibody (Cappel, West Chester, Pa.). After an additional 30 min, the cells were washed and analyzed for fluorescence intensity using a Meridian ACAS anchored cell analysis system. A) Upper left, untreated control cells; B) upper right, cells treated for 48 h with LPS (100 ng/ml) and γIFN (100 U/ml); C) lower left, cells treated for 48 h with OPN (100 pM); D) lower right, cells treated for 48 h with LPS, γIFN and OPN. The color bar represents relative fluorescence intensity on the four-decade log scale with white being the most intense.
Figure 4B:
Figure 4C:
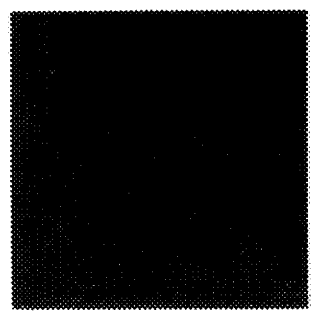
Figure 4D:
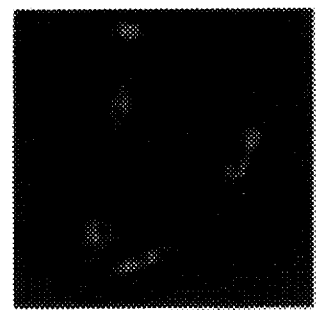

Inhibition of NO production by OPN. Recombinant human OPN was found to lower iNOS mRNA induction (measured at 8 h, FIG. 3A) and nitrite production (measured at 24 h, FIG. 3B) in subconfluent PTE cells treated with LPS and γ-IFN. Concentrations of 1 and 100 pM OPN, respectively, added simultaneously with the inducers, reduced the level of the 4 kb mRNA species to 54% and 31% (normalized to 18 S rRNA) and nitrite production to 45% and 24% (relative to the LPS and γ-IFN-stimulated cells). The two larger mRNA species detected in the northern blot may result from the utilization of alternative polyadenylation sites (Ishii et al., 1991, J. Pharmacol. Exp. Therap., 256:38–43). The diminished concentration of iNOS protein in the OPN-treated stimulated cells is obvious in FIG. 4.

Figure 5A:
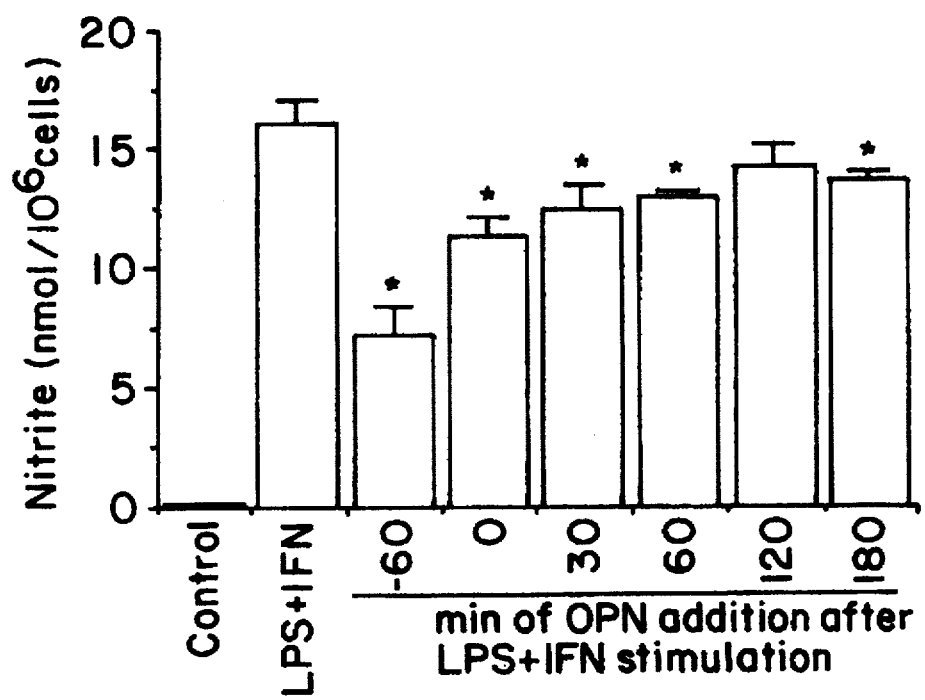
FIGS. 5A and 5B. Time-dependence and antiserum-sensitivity of OPN-mediated down-regulation of NO production. Values are the mean±standard error from three separate plates. The asterisks indicate a statistically significant difference from the stimulated cells at a confidence level p<0.02. A) OPN (100 pM) was added at the indicated time prior to or after stimulation with LPS and γIFN; nitrite was measured after 24 h. B) Treatment with a 1/10$^5$ dilution of the anti-OPN antiserum LF7. Antiserum and OPN were incubated together at 25° C. for 10 min prior to adding to the medium.
Figure 5B:
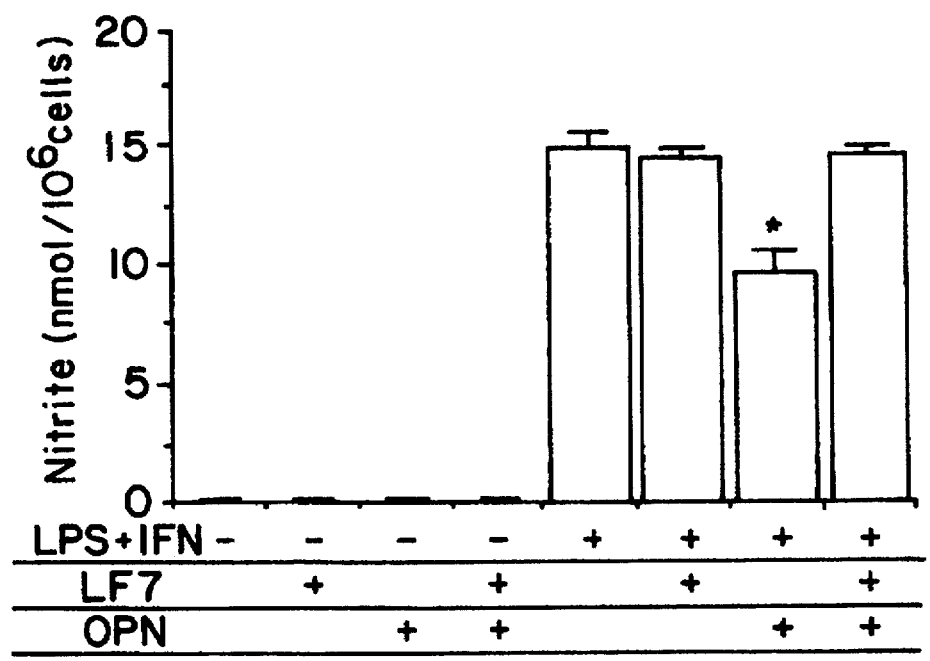

The results shown in FIG. 5A indicate that OPN added 60 min prior to the addition of γ-IFN and LPS was more inhibitory than when added simultaneously with these NO inducers. Inhibition of NO production decreased as the time between the addition of LPS and γ-IFN, and OPN, increased. FIG. 5B shows that an antiserum raised against OPN purified from human bone blocked the ability of OPN to suppress the induction of NO synthesis by these cells. The preparation of OPN used in this experiment (and FIG. 6) was not quite as active as that used in the experiments described in FIGS. 2 and 3 because of some loss of activity during storage.

Evidence that an integrin receptor mediates OPN's effect on NO induction. To identify the receptor for OPN, the ability to certain peptides to mimic, or inhibit, the action of OPN on induced NO production was evaluated. Recent studies have indicated that the cell adhesion propertied of OPN are mediated via a GRGDS sequence in the protein that interacts with the $\alpha_v\beta_3$ integrin (Flores et al., 1992, Exp. Cell. Res. 201:526–530; Ross et al., 1993, J. Biol. Chem. 269:9901–07). This experiment investigated whether an RGD-dependent integrin may also mediate the ability of OPN to inhibit NO production.

Figure 6A:
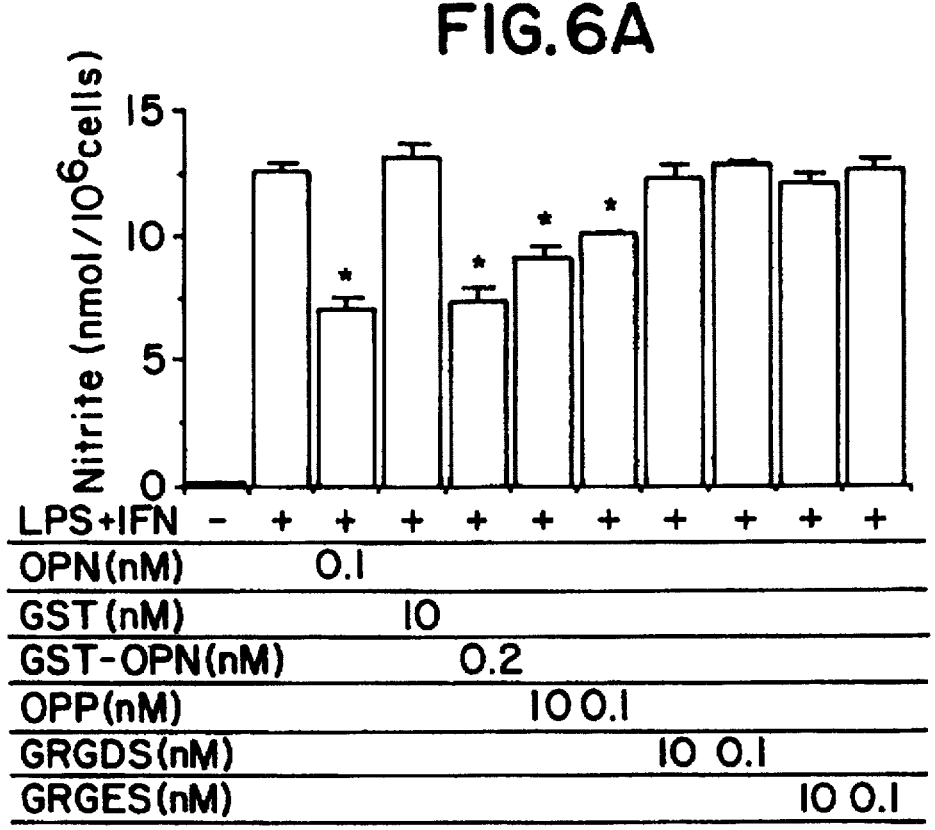
FIGS. 6A and 6B. Effect of OPN, GST-OPN, OPP, GRGDS (SEQ ID NO: 1), and GRGES (SEQ ID NO: 3) on nitrite production. Cells were stimulated and nitrite measured as described above. Values are the mean±standard error from three separate plates. A) Effect of each agent alone on nitrite production by the stimulated cells. All concentrations are expressed as nM. GST, glutathione-S-transferase. B) Ability of GRGDS (SEQ ID NO: 1) but not GRGES (SEQ ID NO: 3) to reverse the OPN-mediated inhibition of nitrite production by stimulated cells. Concentrations are as indicted. The asterisks indicate a statistically significant difference from the stimulated cells at a confidence $p<0.1$.

FIG. 6A shows that both GST-OPN (a fusion protein between glutathione-S-transferase and human OPN made in *E. coli*) and OPP (a synthetic 20 amino-acid peptide that represents the sequence centered on the RGD sequence of OPN) were also effective at reducing LPS and γ-IFN-induced NO production. The pentapeptides GRGDS (SEQ ID NO: 1) and GRGES (SEQ ID NO: 3) did not show any effect on NO production up to 10 nM.

Figure 6B:
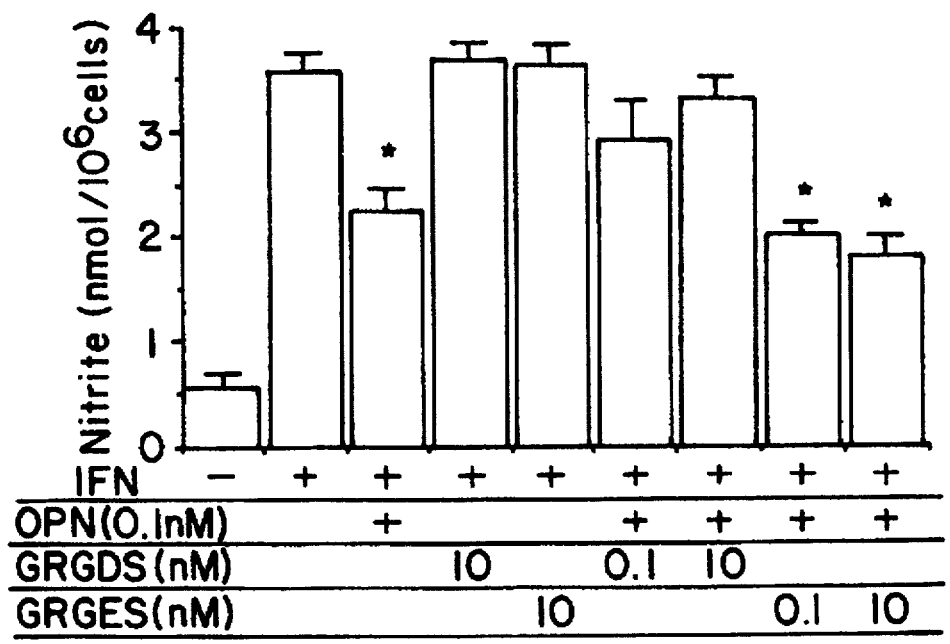

FIG. 6B shows that GRGDS (SEQ ID NO: 1), but not GRGES (SEQ ID NO: 3), was able to reverse the OPN-mediated suppression of γ-IFN-induced NO production. Nitrite production was less in this experiment compared to that in 6A because the cells were stimulated only with γ-IFN. A 100-fold molar excess of GRGDS (SEQ ID NO: 1) blocked the action of OPN, whereas the same concentration of GRGES (SEQ ID NO: 3) had no effect.

These results are in harmony with the idea that OPN is acting via an integrin, presumably the $\alpha_v\beta_3$ integrin, to inhibit the induction of iNOS. The $\alpha_v\beta_3$ integrin has been localized to the basolateral surface of tubule epithelial cells in the mouse kidney (Lopex et al., 1993, Lab Invest).

Discussion

The above data establish (1) that γ-IFN and LPS stimulate NO production in renal epithelial cells by inducing expression of the iNOS gene, and (2) that OPN inhibits the elevation of NO synthesis that is caused by these inflammatory mediators by suppressing induction of iNOS gene expression. The experiments described in FIGS. 5 and 6 in particular show that an anti-OPN antiserum and the GRGDS (SEQ ID NO: 1) peptide, but not GRGES (SEQ ID NO: 3), could reverse the OPN-mediated suppression of NO induction. They also show that both a peptide homologous to a 20 amino acid segment of OPN, including the RGD site in OPN, and a GST-OPN fusion protein purified from *E. coli* were also able to inhibit NO synthesis. This is interesting not only because it strengthens conclusions about the action of OPN on NO production, but also because it suggests that the post-translational modifications characteristic of the OPN protein made in mammalian cells are unnecessary for this apparently integrin-mediated down-regulation.

OPN was effective on the subconfluent PTE cells used in this work at surprisingly low concentrations (~10 pM). Effects on confluent cells required higher concentrations, a situation that may more closely reflect the situation in the intact organ. Zimolo et al. (1993, Amer. J. Physiol.), have shown that OPN (purified from urine) at concentrations as low as 1 pM could raise the intracellular free $Ca^{++}$ level in osteoclasts. For reasons unknown, this conflicts with an earlier report (Miyauchi et al., 1991, J. Biol. Chem., 266:20369–74) that much higher concentrations of OPN purified from bone lowered $Ca^{++}$ levels.

Certain events in the signal transduction pathway may be responsible for the observed effect of OPN on iNOS gene expression. Integrins, upon ligand binding, have the capacity to interact with cytoskeletal components, and preliminary evidence indicating that phosphorylation of the focal adhesion kinase occurs upon OPN binding. Thus it may be that a cascade of phosphorylation events results in the down regulation of iNOS expression. It is possible that changes in OPN level in the renal interstitial fluid, for example during inflammation, could modulate NO production and thereby control blood flow through the kidney. NO is an important vasodilator in the kidney (Brelis et al., 1991, J. Clin. Invest. 88:390–395; Wilcox et al., 1992, Proc. Natl. Acad. Sci. U.S.A. 89:11993–97, Stoos et al., 1992, J. Clin. Invest. 89:761–765; Ishii et al., 1991, J. Pharmacol. Exp. Therap. 256:38–43; Markewitz et al., 1993, J. Clin. Invest. 91:2138–2143). OPN expression in the kidney is curiously focal in that only a subset of nephrons express it a high level at any one time (Lopez et al., supra); Giachelli et al. (1993, Kidney Int.) have observed that in angiotensin II-induced tubulointerstitial nephritis there are focal increases in OPN levels that precede overt pathological changes in regions that correlate with sites of macrophage accumulation.

There are several ways in which the OPN-mediated down-regulation of NO biosynthesis could be of physiological significance in the renal tubule epithelium. For example, NO production is important in regulating blood flow (Brezis et al., supra) and ion transport (Stoos et al., supra), and consequently blood volume and osmolality. NOS is abundant in the macula dense, consistent with the belief that these tubular epithelial cells adjacent to the afferent arteriole of cortical nephrons regulate glomerular capillary pressure and the tubuloglomerular feedback response, including renin release via NO production (Wilcox et al., supra). Localization of the OPN receptor on the basolateral surface of the tubule cells is consistent with their being subject to regulation by interstitial OPN. Glomerulonephritis, induced for example by the accumulation of immune complexes and the consequent infiltration of neutrophils and activated macrophages, is characterized by the enhanced production of NO, which may contribute to the tissue injury (Cattel et al., 1990, Kidney Int. 38:1056–60; Cook and Moncada, 1991, Am. J. Pathol. 39:1042–52).

During inflammation or stress-related processes such as reperfusion injury, kidney cells are exposed to an array of inflammatory mediators and paracrine factors derived not only from the epithelial tissue but also from infiltrating macrophages, granulocytes and lymphocytes. Many of these factors, in particular γ-IFN, IL-1β, and TNF-α, stimulate NO production in mesangial cells (Ishii et al., supra). Excessive NO and related reactive nitrogen intermediates, as well as reactive oxygen intermediates, are cytotoxic, damaging the epithelium and compromising kidney function. Lipid peroxidation reactions generated by the reactive oxygen and nitrogen intermediates are known to damage cell membranes. Thus, OPN localized in the kidney may serve not only to regulate renal homeostatic processes, but also to protect the organ against NO-induced cell injury. Enhanced NO production is a serious consequence of uremia (Noris et al., 1993, Kidney Int. 44:445–450), and to the extent to which OPN can ameliorate this pathological condition, it will be an important therapeutic agent.

NOS mRNA abundance increases during hypoxia but then decreases upon subsequent reperfusion of primary human PTE cells in culture (data not shown). How a transient increment in NO production impacts on the survival of the hypoxic cell is not known, but one possibility is that by means of guanylyl cyclase activation, beneficial changes in $Ca^{++}$ levels and gene expression are effected.

Given the known cytotoxicity of NO, it is likely that rapid and effective down-regulation of NO production is necessary for the survival of the tubule cell. Thus, it is interesting that OPN expression was augmented not only during hypoxia but also, and even more so, during subsequent reperfusion. Elevated expression of OPN, or administration of OPN, and consequent down-regulation of NO production, may be necessary for minimizing ischemic injury in the kidney and other organs.

EXAMPLE 2

The Example above describes the induction of the iNOS form of NOS in PTE cells by the inflammatory mediators LPS and γ-IFN, and inhibition of iNOS induction by osteopontin and the 20-amino acid fragment of osteopontin. This example concerns the novel and unexpected discovery that treatment with angiotensin peptide (A II) and ionomycin not only increases NO production but also enhances constitutive nitric oxide synthase (cNOS) mRNA abundance in mouse primary kidney proximal tubule epithelial (PTE) cells, and that osteopontin (OPN) opposes the increase in NO synthesis mediated by cNOS.

Materials and Methods

Preparation of Cells. CD-1 mice aged 4–6 weeks were obtained from Laboratory Animal Services of Nelson Biological Laboratory, Rutgers University, New Jersey. Primary mouse kidney proximal tubule epithelial (PTE) cells were prepared as previously described in Example 1. For NO measurement, cells were subcultured into 24-well tissue culture plates (Linbro, Hamden, Conn.) at $5 \times 10^4$ cells per well and incubated overnight for cell attachment. After removal of the medium, the cells were washed twice with Dulbecco's phosphate buffered saline (0.2 g/l KCl, 0.2 g/l $KH_2PO_4$, 8 g/l NaCl, 1.15 g/l $Na_2HPO_4$) and re-fed phenol red-free RPMI 1640 medium (Gibco) containing 10 μg/ml tetrahydrobiopterin (ICN Biochemicals, Cleveland Ohio).

Recombinant human osteopontin (OPN) was prepared from a human embryonic kidney cell, NOIL, as described in Example 1. Angiotensin II and ionomycin were obtained from Sigma Chemical Co. (St. Louis, Mo.). N-monomethyl-L-arginine (L-NMA) was from BIOMOL Research Laboratory Inc. (Plymouth Meeting, Pa.).

Measurement of NO Production. Synthesis of NO in the medium over a 3-day period was determined by the accumulation of nitrite, a stable oxidized product of NO (Marletta, 1988, Chem. Res. Toxicol. 1:249–257). Nitrite was measured with the Griess reagents using sodium nitrite as standard, as described in Example 1.

Northern Blot Analysis. Total RNA was isolated using TRI reagent (Molecular Research Center, Cincinnati, Ohio) after 12 h stimulation in the medium (see Example 1). Rat brain constitutive nitric oxide synthase (cNOS) cDNA was obtained as described (Bredt et al., 1991, Nature 351:714–718). Five μg of total RNA was separated on an agarose-formaldehyde gel, transferred onto a nylon membrane (GeneScreen Plus, NEN Research Products, Du Pont, Boston, Mass.) and hybridized with a $^{32}$P-labeled cNOS cDNA probe. The blot was washed 3 times with 0.5×SSC, 0.1% SDS at 65° C. and autoradiographed for 1 to 3 days. The membrane was stripped and successively hybridized to a mouse 18S rRNA probe. The relative intensities of cNOS to 18S rRNA in the resulting autoradiograms were quantified by densitometry (Pharmacia LKB, UltraScan XL).

Measurement of intracellular calcium mobilization. Primary mouse PTE cells were subcultured onto collagen-coated Nunc coverglass chambers (Nunc, Inc., Naperville, Ill.). Intracellular calcium mobilization was monitored using a fluorescent, calcium-sensitive indicator Indo-1-acetoxymethyl ester (Indo-1 AM) (Molecular Probes, Eugene, Oreg.) and qualified on a Meridian 570 Anchored Cell Analysis (ACAS) equipped with an Innova 90-5W laser adjusted to an output of 100 mW. Cells were washed with HBSS containing 0.3% bovine serum albumin (BSA) and incubated with 1 μM Indo-1 AM at 37° C. for 30 min. Then, the cells were washed 3 times and 1 ml of HBSS containing 0.3% BSA was added. The calcium ratio was determined by scanning single 150×150 μm field containing about 10 cells every 30 sec for a total of 10 min and recording the emission at 500 nm (calcium-free Indo-1) and 400 nm (calcium-saturated Indo-1). Intracellular calcium concentrations were determined by generating a standard curve using a known calcium solution (Gardner et al., 1993, J. Leukocyte Biol. 53:190–196). All data were analyzed with Meridian ACAS statistical software.

Nuclear Run-on Analysis. Nuclei were isolated from primary mouse PTE cells ($10-20 \times 10^6$ cells) as described (Greenberg and Bender, 1989, In Current Protocols in Molecular Biology, Ausubel et al. (Eds.), John Wiley & Sons: New York, pp. 4.10.1–4.10.9). For run-on reactions, freshly thawed nuclei were incubated in transcription buffer (5 mM Tris-HCl, pH 8.0, 2.5 mM $MgCl_2$, 150 mM KCl, 0.5 mM each of ATP, CTP, GTP and 2 mM dithiothreitol) containing 10 U/ml RNasin ribonuclease inhibitor (Promega Corp., Madison, Wis.) and 100 μCi α[$^{32}$P]UTP (800 mCi/mmol, Amersham Corp., Arlington Heights, Ill.) at 30° C. for 30 min. The reaction was stopped by addition of 40 U of RNase-free DNase (Promega) at 30° C. for 10 min. The labeled transcripts were isolated by addition of 5 volumes of TRI reagent following the RNA extraction protocol. Equal amounts of [a$^{32}$P]RNA probes were hybridized to mouse macrophages inducible nitric oxide synthase (iNOS) cDNA, cNOS cDNA, mouse β-actin cDNA and mouse glyceraldehyde-3-phosphate dehydrogenase (GAPD) cDNA, which had been slot-blotted onto a nylon membrane (500 ng/slot) (GeneScreen Plus). Prehybridization (55° C. 12 h) and hybridization (55° C., 48 h) were performed in glass scintillation vials with the same solution (50% formamide, 40 mM Na$_2$HPO$_4$ pH 6.5, 0.8M NaCl, 1 mM EDTA pH 8.0, 5× Denhardt's solution, 1% SDS, and 250 μg/ml sheared salmon sperm DNA). Blots were washed 3 times with 50 mM NaCl, 20 mM Na$_2$HPO$_4$ pH 6.5, 1 mM EDTA and 0.1% SDS at 60° C. for 15 min and exposed to X-Ray films at 70° C. with intensified screens. The relative intensities of the resulting autoradiograms were quantified by densitometry.

Results and Discussion

Figure 7:
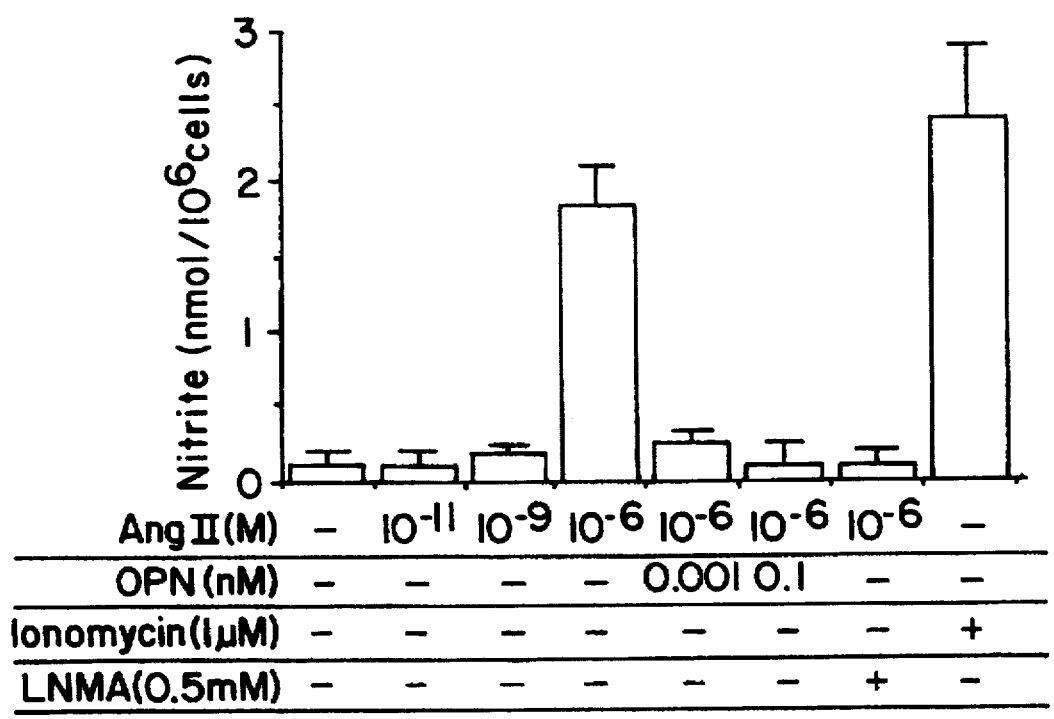
FIG. 7. Angiotensin II enhances nitrite production by a process that can be reversed by OPN in PTE cells. Primary mouse kidney proximal tubule epithelial cells were grown as described in the Examples, infra. Cell were cultured and the medium collected after three days of growth in medium with the indicated supplements.
Figure 8A:
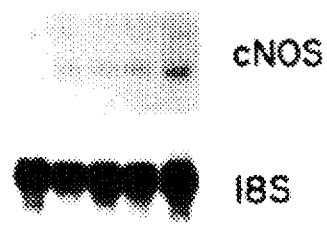
FIGS. 8A and 8B. Northern blot analysis of constitutive nitric oxide synthase (cNOS) mRNA expression. (A) Autoradiogram of RNA separated by agarose-formaldehyde gel electrophoresis, transfered to nylon membranes, and probed with $^{32}$P-labelled oligonucleotide probes as described in Example 2, infra. (B) Reltive intensities of cNOS to 18S rRNA quantified by densitometry. Cells were treated with buffer, angiotensin (1 μM), angiotensin with osteopontin (0.1 and 0.001 nM), or ionomycin, as indicated in B. The blots in (A) correspond to the bars in (B).

A II stimulates PTE cells to make NO by an OPN-sensitive process. Incubation of mouse primary kidney PTE cells for 3 days with different concentrations of A II followed by measurement of nitrite revealed a dose-dependent increase in nitrite accumulation (FIG. 7). Ionomycin, a calcium ionophore, also increased nitrite production in these cells. Osteopontin (OPN), a suppressor of inducible nitric oxide synthase (iNOS) gene expression, almost completely blocked the A II-induced augmentation of nitrite production. N-monomethyl-L-arginine (L-NMA), an inhibitor of NO synthesis, inhibited the nitrite production induced by A II. This indicates that nitrite was a metabolite from an arginine-dependent process, almost certainly NO synthesis.

cNOS mRNA levels in A II-and OPN-treated mouse PTE cells. Northern blot analysis of total RNA isolated from A II stimulated mouse primary PTE cells with or without OPN for 12 h revealed a 5 kb band (FIG. 8A). This species was detected by the rat brain constitutive nitric oxide synthase (cNOS) cDNA probe, but not by the mouse macrophage iNOS cDNA probe (not shown). The position of this band above the 28S rRNA marker (FIG. 8A) made it easy to distinguish from the cytokine-induced macrophage-like iNOS mRNA, which was around 4 kb and below the 28S rRNA band.

Figure 8B:
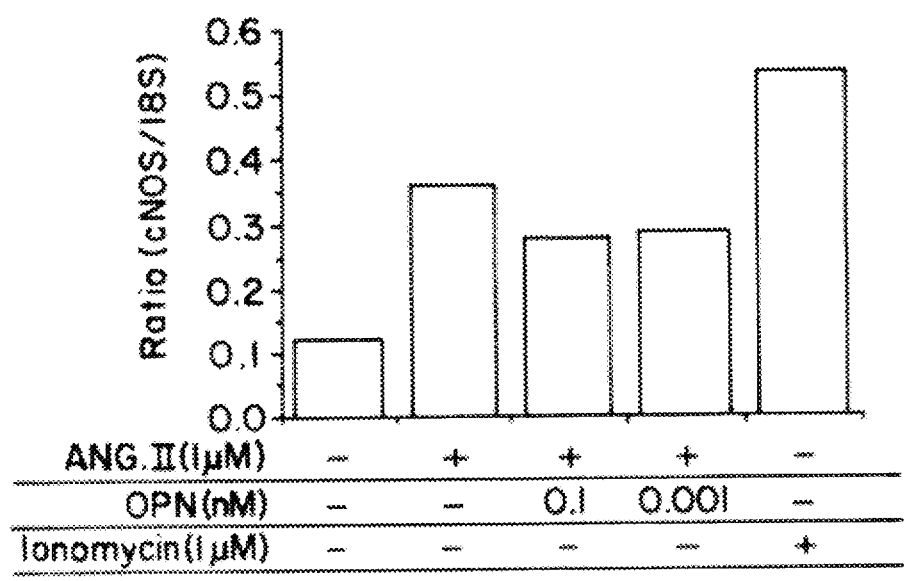

The Norther analysis bands were quantitated using densitometry, and the ratio of iNOS:28S rRNA determined so that the relative expression of iNOS mRNA could be compared from one sample to another (FIG. 8B). A II enhanced cNOS mRNA by 3.5 fold. Addition of OPN (0.1 nM or 1 pM) had only a modest effect on the amount of A II-induced cNOS mRNA. Interestingly, ionomycin could also greatly increase the cNOS mRNA abundance in mouse primary PTE cells.

Figure 9A:
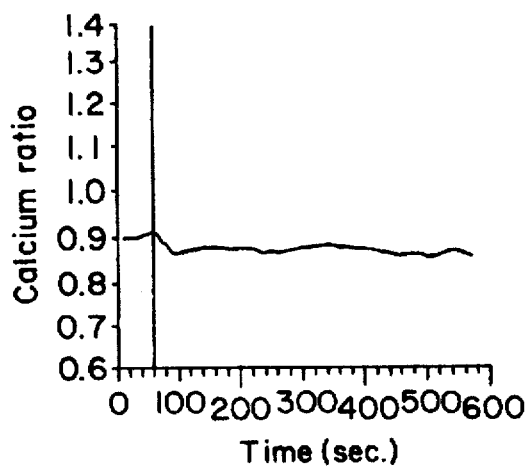
FIGS. 9A–D. Induction of calcium mobilization by ionomycin, angiotensin II and osteopontin in PTE cells. Cells were incubated with 1 μM Indo-1 AM [1-(2-amino-5-(6-carboxyindol-2-yl)phenoxy)-2-(2'-amino-5'-methylphenoxy)ethane-N,N,N',N'-tetraacetic acid) and analyzed on a Meridian 570 Anchored Cell Analysis System (ACAS) equipped with an Innova 90 5-W laser adjusted to an output of 100 mW. Calcium mobilization was quantified by scanning single 150×150 μm fields containing about 10 cells every 30 s for a total of 10 min and quantifying the emission at 500 nm (calcium-free Indo-1) and 400 nm (calcium-bound Indo-1). After 1 min, the cells were stimulated with (A) control, (B) 10 μM ionomycin, (C) 0.1 mM angiotensin II, and (D) 2 nM or 0.1 nM OPN.
Figure 9B:
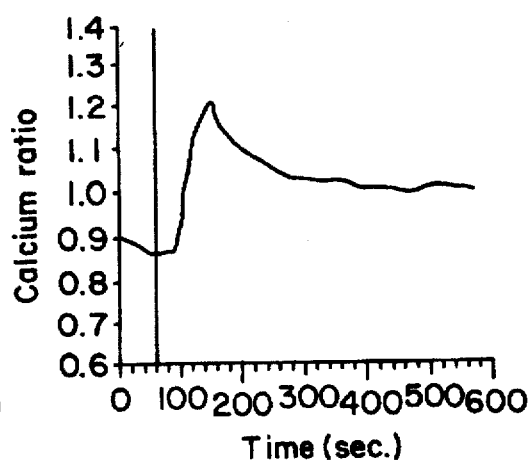
Figure 9C:
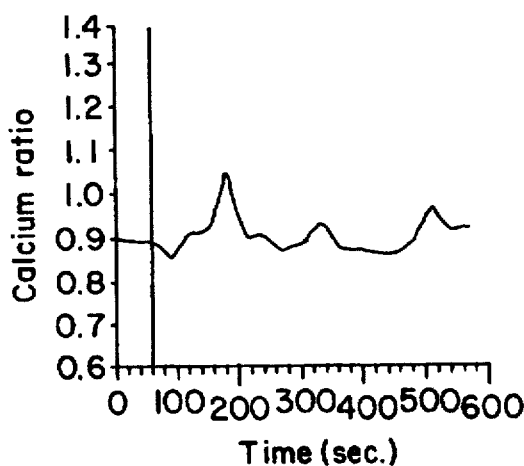
Figure 9D:
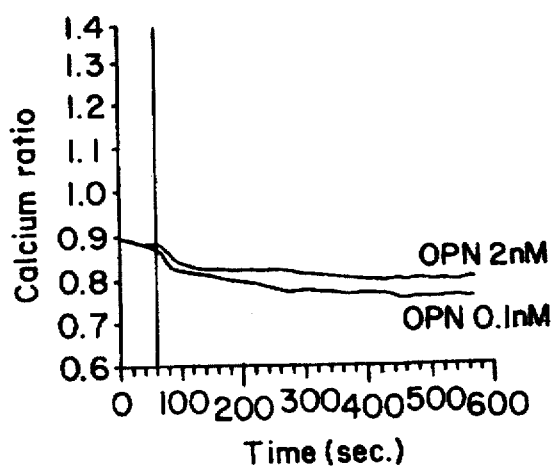

Calcium mobilization in mouse PTE cells. In order to investigate the functions of OPN involving in the A II-stimulated mouse primary PTE cells, the effects of A II and OPN on the intracellular calcium mobilization in these cells were analyzed by fluorescence image analysis system (FIG. 9). In initial experiments, addition of 1 μM of A II to the mouse PTE cells induced only a delayed and small transient response in calcium mobilization within 10 min (not shown). When 0.1 mM of A II was added onto the cells, a fast and transient rise in cytosolic free calcium levels was induced (FIG. 9C). Ionomycin induced an immediate calcium influx by opening calcium channels, resulted in an increase in cytosolic free calcium (FIG. 9B). In contrast, a significantly different pattern of calcium mobilization, specifically a reduction in the cytosolic free calcium, was found by adding OPN onto the cells (FIG. 9D). Interestingly, the smaller concentration of OPN was more potent in reducing calcium levels.

Although A II has been recognized as a vasoconstrictic agent, it has a variety of functions, which include promoting hypertrophy or proliferation in different cells and tissues. It stimulates the early growth response genes, Egr-1 and c-fos, in kidney (Rosenberg and Hostetter, 1993, Kidney Int. 43:601–609); stimulates proliferation (cellular hypertrophy) and biosynthesis of type I collagen in mesangial cells (Wolf et al., 1991, Cell Regulation 2:219–227); and increases transcription and secretion of type IV collagen in PTE cells (Wolf et al., 1992, Am. J. Pathol. 140:95–107). It increases OPN expression in arterial smooth muscle cells (Giachelli et al., 1993, J. Clin. Invest.), inducing vascular smooth muscle hypertrophy. A II also induces secretion of plasminogen activator inhibitor 1 and tissue metalloproteinase inhibitor from rat brain astrocytes (Olson et al., 1991, Proc. Natl. Acad. Sci. U.S.A. 88:1928–32). Chaki and Inagami (1993, Mol. Pharmacol. 43:603–608) observed that angiotensin II and ionomycin could stimulate cGMP formation in the mouse neuroblastoma cell line Neuro2a and NO synthesis, perhaps by Ca influx. This example shows that A II can enhance cNOS mRNA levels in mouse primary PTE cells.

Norman et al. (1987, Am. J. Physiol. 253:F299–F309) reported that a high concentration ($5\times10^6$M) of A II was necessary to induce a transient rise in cytosolic free calcium concentration in primary cultures of rabbit kidney PTE cells. Because cNOS is a calcium- and calmodulin-dependent enzyme (Bredt and Synder, 1990, Proc. Natl. Acad. Sci. U.S.A. 87:682–685), a high concentration of A II seemed to be required to increase NO production in these cells.

The biochemistry underlying the reduction of NO production by OPN remains to be worked out. Recent observations indicate that when OPN interacts with its cell surface receptor, presumably the $\alpha_v\beta_3$ integrin, transient changes in the phosphorylation of various intracellular proteins on tyrosine residues can be detected. Miyauchi et al. (1991, J. Biol. Chem. 266:20369–74) have demonstrated that OPN could precipitate a reduction in cytosolic free calcium by activating the plasma membrane Ca2+-ATPase in a calmodulin-dependent reaction in chicken osteoclast. In contrast, Zimolo et al. (1993, Am J. Physiol.) observed that OPN triggered a transient rise in intracellular $Ca^{++}$ in rat osteoclast. In mouse primary PTE cells, OPN caused a reduction in cytosolic $Ca^{++}$ by an unknown mechanism.

The results of these experiments demonstrate that OPN does significantly reduce angiotensin II-mediated NO production. Preliminary data suggest that this reduction in NO production does not correlate with regulation of cNOS expression, as OPN likely does not have an effet on cNOS mRNA or protein levels. Instead, OPN may possibly reduce NO production through its influence on $CA^{2+}$ levels. Activity of cNOS depends on calcium.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

It is also to be understood that all molecular weight information for molecules, in particular proteins and polypeptides, are approximate and are used for the purpose of description.

Various references are cited throughout this specification, each of which is incorporated herein by reference in its entirety.

What is claimed is:

1. A method for treating an inflammatory disease or disorder in an animal subject mediated by an activity of nitric oxide comprising administering a molecule to an animal subject suspected of having an inflammatory disease or disorder involving an activity of nitric oxide in an amount sufficient to inhibit nitric oxide production, which molecule
   a) is characterized by the presence of an epitope found on osteopontin comprising an amino acid sequence glycine-arginine-glycine-aspartic acid-serine (SEQ ID NO:1),
   b) has a molecular weight of at least 2145 Daltons,
   c) has the structure of a region of osteopontin corresponding in size to the molecular weight of the molecule, containing the glycine-arginine-glycine-aspartic acid-serine (SEQ ID NO: 1), and
   d) inhibits nitric oxide production.

2. The method according to claim 1 in which the molecule is a polypeptide.

3. The method according to claim 2 in which the polypeptide has about 20 amino acid residues, including a five-amino acid sequence glycine-arginine-glycine-aspartic acid-serine (SEQ ID NO: 1).

4. The method according to claim 3 in which the polypeptide has an amino acid sequence as follows:
   proline-threonine-valine-aspartic acid-valine-proline-aspartic acid-glycine-arginine-glycine-aspartic acid-serine-leucine-alanine-tyrosine-glycine-leucine-arginine-serine-leucine (SEQ ID NO: 2).

5. The method according to claim 4 in which the N-terminus of the peptide is protected.

6. The method according to claim 2 in which the polypeptide is osteopontin.

7. The method according to claim 1 in which the molecule suppresses the expression of inducible nitric oxide synthase (iNOS).

8. The method according to claim 1 in which the molecule suppresses the activity of constitutive nitric oxide synthase (cNOS).

9. The method according to claim 1 in which the inflammatory disease or disorder is mediated by a molecule selected from the group consisting of γ-interferon and lipopolysaccharide.

10. The method according to claim 1 in which the inflammatory disease or disorder is selected from the group consisting of ischemia, septic shock, and cell mediated immune response.

11. The method according to claim 1 in which the inflammatory disease or disorder is located in the inner ear or the kidney.

12. A method for treating a disease or disorder in an animal subject involving an activity of nitric oxide comprising administering a compound capable of inducing expression of native osteopontin in an amount effective to induce expression of osteopontin, which osteopontin is expressed in an amount sufficient to inhibit nitric oxide production, to an animal subject suspected of having a disease or disorder involving an activity of nitric oxide.

13. A molecule effective to inhibit nitric oxide production, which molecule:
   a) is characterized by containing an epitope found on osteopontin consisting of an amino acid sequence glycine-arginine-glycine-aspartic acid-serine (SEQ ID NO: 1),
   b) has a molecular weight of at least 2145 Daltons and not greater than about 10,000 Daltons,
   c) has the structure of a region of osteopontin corresponding in size to the molecular weight of the molecule, containing the glycine-arginine-glycine-aspartic acid-serine (SEQ ID NO: 1), and
   d) inhibits nitric oxide production.

14. The molecule of claim 13 which is a polypeptide.

15. The molecule of claim 14 in which the polypeptide has about 20 amino acid residues, including a five-amino acid sequence glycine-arginine-glycine-aspartic acid-serine (SEQ ID NO: 1).

16. The molecule of claim 15 in which the polypeptide has an amino acid sequence as follows:
   proline-threonine-valine-aspartic acid-valine-proline-aspartic acid-glycine-arginine-glycine-aspartic acid-serine-leucine-alanine-tyrosine-glycine-leucine-arginine-serine-leucine (SEQ ID NO: 2).

17. The molecule of claim 16 in which the N-terminus of the peptide is protected.

18. A pharmaceutical composition comprising the molecule of claim 13 and a pharmaceutically acceptable carrier.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
  ( A ) ORGANISM: Homo sapiens ( x i ) SEQUENCE DESCRIPTION: SEQ ID NO:1:

```
Gly  Arg  Gly  Asp  Ser
1                    5
```

( 2 ) INFORMATION FOR SEQ ID NO:2:

( i ) SEQUENCE CHARACTERISTICS:
  ( A ) LENGTH: 20 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
  ( A ) ORGANISM: Homo sapiens ( x i ) SEQUENCE DESCRIPTION: SEQ ID NO:2:

```
Pro  Thr  Val  Asp  Val  Pro  Asp  Gly  Arg  Gly  Asp  Ser  Leu  Ala  Tyr  Gly
1                   5                        10                       15
Leu  Arg  Ser  Leu
               20
```

( 2 ) INFORMATION FOR SEQ ID NO:3:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
  ( A ) ORGANISM:

( x i ) SEQUENCE DESCRIPTION: SEQ ID NO:3:

Gly Arg Gly Glu Ser
1               5